United States Patent [19]
Reilly et al.

[11] Patent Number: 5,916,197
[45] Date of Patent: *Jun. 29, 1999

[54] INJECTION SYSTEM, PUMP SYSTEM FOR USE THEREIN AND METHOD OF USE OF PUMPING SYSTEM

[75] Inventors: David M. Reilly; Alan D. Hirschman, both of Glenshaw, Pa.

[73] Assignee: Medrad, Inc., Indianola, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/801,706

[22] Filed: Feb. 14, 1997

[51] Int. Cl.$^6$ .................................................. A61M 5/00
[52] U.S. Cl. ........................................ 604/151; 604/152
[58] Field of Search ........................... 604/30–34, 49–53, 604/65, 67, 131, 135, 143, 151, 152, 153, 191, 154

[56] References Cited

U.S. PATENT DOCUMENTS

| | | |
|---|---|---|
| 3,447,479 | 6/1969 | Rosenberg . |
| 3,949,746 | 4/1976 | Wallach ................................. 604/152 |
| 3,993,061 | 11/1976 | O'Leary ................................. 604/152 |
| 3,994,294 | 11/1976 | Knute ...................................... 604/152 |
| 4,475,666 | 10/1984 | Bilbrey et al. ......................... 604/152 |
| 4,563,175 | 1/1986 | LaFond .................................. 604/155 |
| 4,734,011 | 3/1988 | Hall, Jr. . |
| 4,795,441 | 1/1989 | Bhatt ..................................... 604/191 |
| 4,838,860 | 6/1989 | Groshong et al. . |
| 4,846,797 | 7/1989 | Howson et al. ........................ 604/154 |
| 4,898,579 | 2/1990 | Groshong et al. ...................... 604/67 |
| 5,044,902 | 9/1991 | Malbec . |
| 5,066,282 | 11/1991 | Wijay et al. . |
| 5,192,269 | 3/1993 | Poli et al. ................................ 604/82 |
| 5,237,309 | 8/1993 | Frantz et al. .......................... 604/153 |
| 5,243,982 | 9/1993 | Mostl et al. ........................... 604/153 |

(List continued on next page.)

FOREIGN PATENT DOCUMENTS

| | | |
|---|---|---|
| 2 715 310 A1 | 1/1994 | France . |
| 43 36 336 A1 | 5/1994 | Germany . |
| 0 511 715 | 5/1978 | United Kingdom . |

OTHER PUBLICATIONS

Debiotech Switzerland, Sales Brochure, Lausanne 9, Switzerland, distributed week of Dec. 1, 1996 at the Radiological Society of North American in Chicago, Illinois.

International Search Report for International Application No. PCT/US 98/02027 filed Feb. 5, 1998.

*Primary Examiner*—Ronald Stright, Jr.
*Assistant Examiner*—A. T. Nguyen
*Attorney, Agent, or Firm*—Gregory L. Bradley; Henry E. Bartony; Gretchen Platt Stubenvoll

[57] ABSTRACT

The present invention provides an injection system and a pump system for use therein for pressurizing a liquid medium for injection into a patient. In general, the pump system comprises a pressurizing unit having at least one chamber. Each chamber has disposed therein a pressurizing mechanism to pressurize liquid medium within the chamber. Preferably, the pressurizing mechanism positively displaces the liquid medium through generally linear motion of the pressurizing mechanism within the chamber. Through reciprocating linear motion of the pressurizing mechanism (for example, a piston), the liquid medium is alternatively drawn into the chamber from a source of liquid medium (for example, a container) and forced out of the chamber under a desired pressure. Each chamber comprises an inlet port and an outlet port. The pump system also preferably comprises an inlet port check valve which allows the liquid medium to flow into the chamber through the inlet port, but substantially prevents the liquid medium from flowing out of the chamber through the inlet port. Likewise, the pump system preferably comprises an outlet port check valve which allows pressurized liquid medium to flow out of the chamber through the outlet port, but substantially prevents the liquid medium from flowing into the chamber through the outlet port. Each inlet port is connected to a source of liquid medium. Each outlet port is connected to a common outlet line or channel leading to the patient.

38 Claims, 14 Drawing Sheets

U.S. PATENT DOCUMENTS

| | | | |
|---|---|---|---|
| 5,378,231 | 1/1995 | Johnson et al. | 604/67 |
| 5,411,485 | 5/1995 | Tennican et al. | 604/191 |
| 5,417,667 | 5/1995 | Tennican et al. | 604/191 |
| 5,429,485 | 7/1995 | Dodge | 604/152 |
| 5,454,792 | 10/1995 | Tennican et al. | 604/191 |
| 5,496,273 | 3/1996 | Pastrone et al. | 604/67 |
| 5,529,463 | 6/1996 | Layer et al. | 604/152 |
| 5,609,572 | 3/1997 | Lang . | |
| 5,632,606 | 5/1997 | Jacobsen et al. . | |

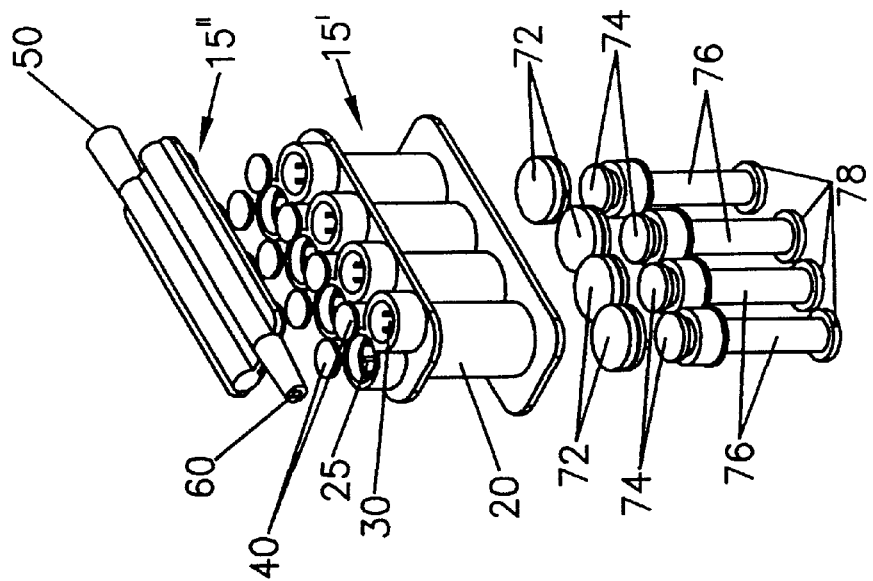
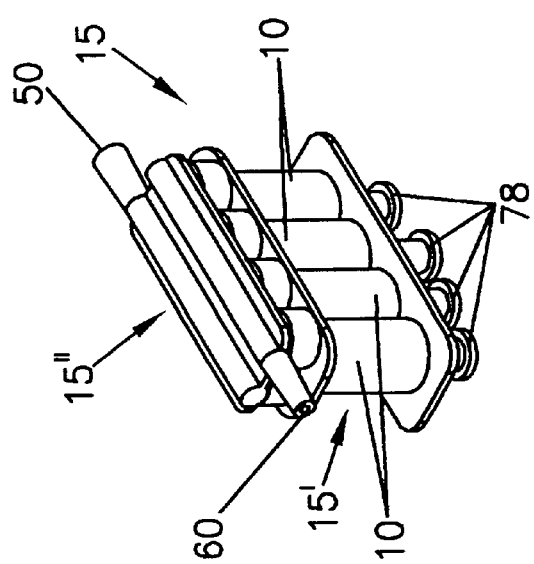
FIG. 1B
FIG. 1A

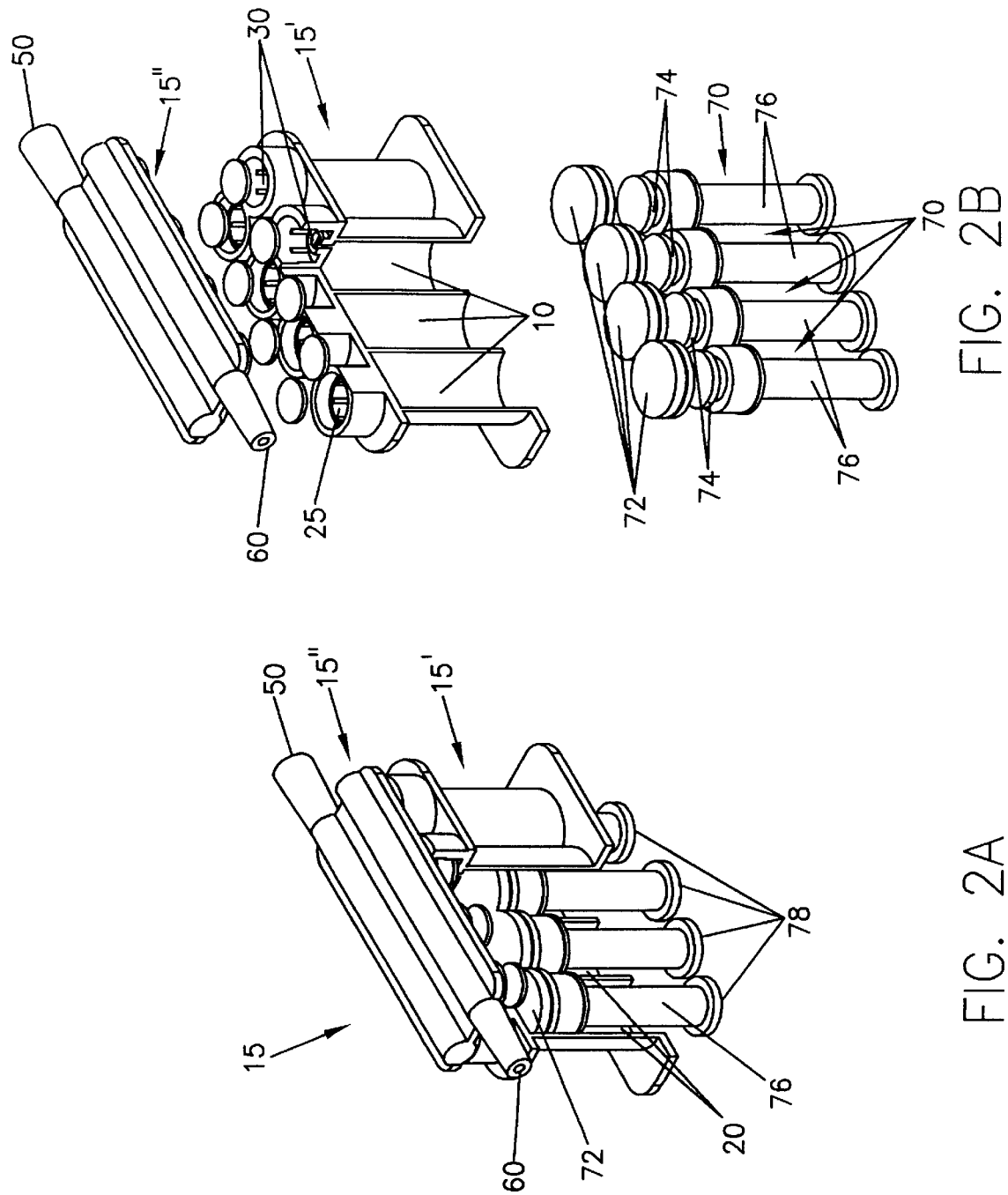

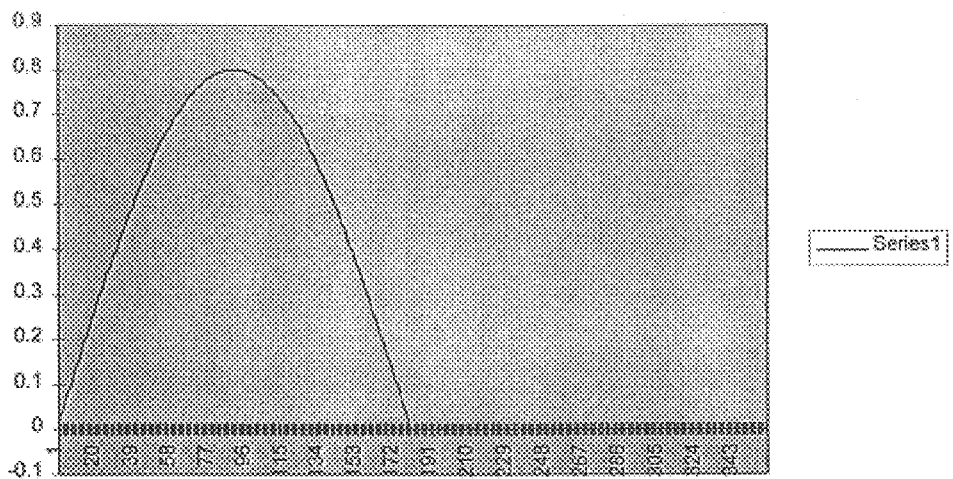
One Cylinder
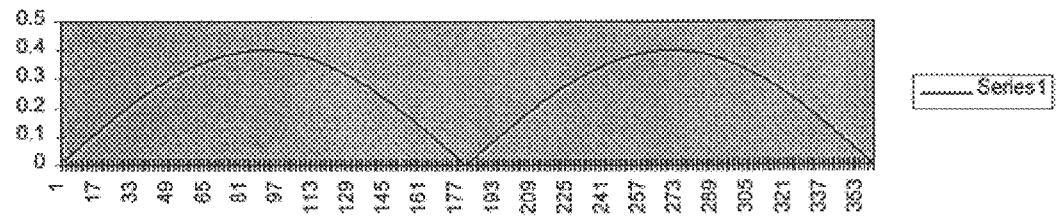
Two Cylinders
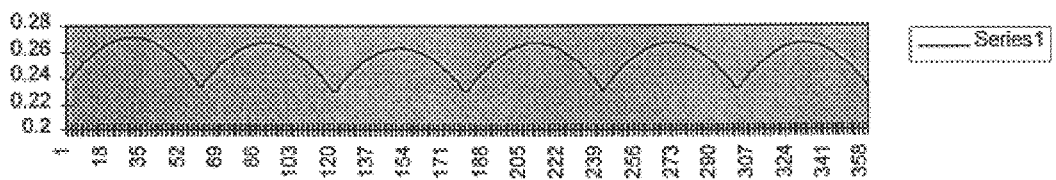
Three Cylinders
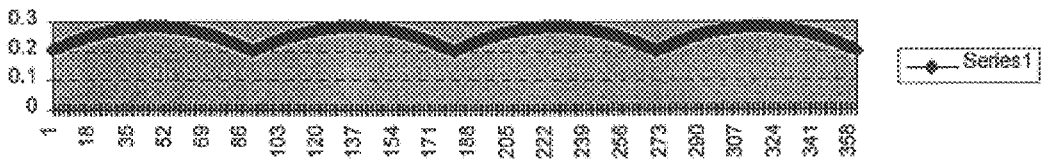
Four Cylinders
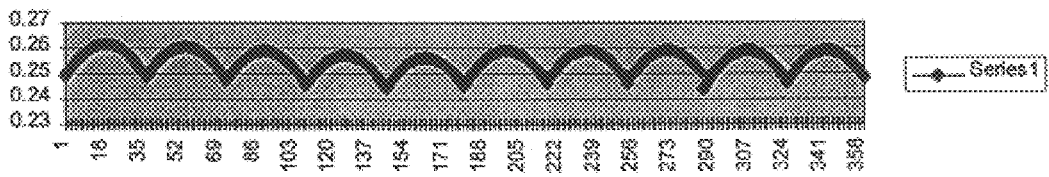
Five Cylinders
FIG. 8B

INJECTION SYSTEM, PUMP SYSTEM FOR USE THEREIN AND METHOD OF USE OF PUMPING SYSTEM

FIELD OF THE INVENTION

The present invention relates to injection systems, to pump systems for use therein and to a method of using such pump systems, and, particularly, to injection systems and to pump systems used to pressurize fluids for use in medical procedures and to a method of using such pump systems.

BACKGROUND OF THE INVENTION

In many medical procedures, such as drug delivery, it is desirable to inject a fluid into a patient. Likewise, numerous types of contrast media (often referred to simply as contrast) are injected into a patient for many diagnostic and therapeutic imaging procedures. For example, contrast media are used in diagnostic procedures such as X-ray procedures (including, for example, angiography, venography and urography), CT scanning, magnetic resonance imaging (MRI), and ultrasonic imaging. Contrast media are also used during therapeutic procedures, including, for example, angioplasty and other interventional radiological procedures. Regardless of the type of procedure, any fluid injected into the patient must be sterile and contain a minimum of pyrogens.

A number of substantial problems arise in the use of current pumping systems and methods for injecting fluid into a patient's body. For example, it is often difficult to accurately control the pressure and flow rate of the fluid exiting the pumping system. In relatively low pressure applications, for example, peristaltic pumps have long been used. However, peristaltic pumps are difficult to control with accuracy.

In the case of relatively high pressure applications, such as CT and angiography, mechanized syringe injectors are used. The use of mechanized syringe injectors also results in a number of substantial drawbacks. Current mechanisms for powering and controlling syringe pumps are complicated, inefficient and costly. Expensive and bulky pressure jackets for housing the syringe pumps are often required to prevent failure at high pressures. Syringe pumps are severely limited in that the maximum volume that can be injected at one time is the volume of the syringe. Disposable syringe pumps are costly. Moreover, the flow rate acceleration of syringe injectors is limited by the inertia of the extensive drive train required to translate motor rotation into syringe plunger motion.

These and other drawbacks in currently available syringe pumping systems create and magnify a number of inefficiencies in current procedures for injecting contrast media. For example, a number of factors, including, but not limited to, the procedure to be performed and the size of the patient, determine: (i) the contrast to be used, (ii) the concentration thereof, and (iii) the amount to be injected. Under current practice of injecting contrast media via syringe pumping systems, hospitals must purchase and stock many contrast media concentrations in multiple container sizes in an attempt to provide the correct concentration and amount of a specific contrast for a specific procedure, while minimizing the wastage of contrast. In that regard, contrast is typically very expensive.

Thus, most contrast media are provided by manufacturers in numerous concentrations in sterilized containers (such as glass bottles or plastic packages) ranging incrementally in size from 20 ml to 200 ml. These containers are generally designed for a single use (that is, once a container is opened for a patient, it is used for that patient only). The contrast is generally aspirated from such containers via the syringe pump used to inject the contrast, and any contrast remaining in the container is discarded to prevent infection with potentially contaminated contrast. The hospital staff is faced with the task of choosing an appropriately sized contrast container to assure an optimum study while minimizing discarded contrast. Time consuming procedures are required to reload the syringe if more contrast is required than originally calculated. On the other hand, expensive waste results if only a portion of a filled syringe is injected. The inventory of contrast containers required under the current system increases costs and regulatory burdens throughout the contrast media supplier-consumer chain.

Many of these costs, regulatory burdens and other problems associated with the use of multiple contrast containers can be substantially eliminated through use of relatively large contrast media containers for single- and multiple-patient use in connection with a pumping system allowing any volume and concentration of contrast to be injected as determined by the hospital staff before or during a procedure. Current syringe pumping systems simply do not provide a sufficiently cost-effective and efficient pumping system to provide optimal pressurization for injection of contrast and other liquid media.

It is, therefore, very desirable to develop injection systems and pump systems that reduce or eliminate the limitations associated with current injection systems and pump systems.

SUMMARY OF THE INVENTION

The present invention provides a pump system for use in pressurizing a liquid medium for injection into a patient. In general, the pump system comprises a pressurizing unit having at least one chamber. The pump system may also include a dampening chamber in fluid connection with the outlet flow of the pump system to decrease the pulsatile nature of the flow.

Each chamber has disposed therein a pressurizing mechanism to pressurize liquid medium within the chamber. Preferably, the pressurizing mechanism pressurizes the liquid medium via positive displacement thereof through generally linear motion of the pressurizing mechanism within the chamber. Through reciprocating linear motion of the pressurizing mechanism (for example, a piston), the liquid medium is alternatively drawn into the chamber from a source of liquid medium (for example, a container) and forced out of the chamber at a desired pressure.

Generally linear, reciprocating motion can be provided by a number of pressurizing mechanisms including, but not limited to, pistons. Generally linear reciprocating motion can also be provided by a flexing element such as a diaphragm disposed within the chamber. In positive displacement of the liquid medium, there is generally a one-to-one correspondence between the length of the generally linear stroke of the pressurizing mechanism and the amount of liquid medium displaced. Positive displacement through generally linear motion provides better volumetric efficiency than achievable through the use of rotational pumps. Volumetric efficiency can be defined as the volume of fluid actually delivered per unit mechanical displacement divided by the theoretical volume of fluid delivered per unit mechanical displacement. The volumetric efficiency of rotational pumps is undesirably dependent upon the pressure and flow rate of the liquid medium.

Each chamber comprises an inlet port and an outlet port. The pump system also preferably comprises an inlet port check valve in fluid connection with each inlet port which allows the liquid medium to flow into the chamber through the inlet port, but substantially prevents the liquid medium from flowing out of the chamber through the inlet port. Likewise, the pump system preferably comprises an outlet port check valve in fluid connection with each outlet port which allows pressurized liquid medium to flow out of the chamber through the outlet port, but substantially prevents the liquid medium from flowing into the chamber through the outlet port. Each inlet port is connected to a source of liquid medium. Each inlet port can be connected (i) to a common source of liquid medium, or (ii) to different sources of varying liquid mediums in the case that mixing of varying liquid mediums is desired. If the volume displaced in each stroke is maintained relatively small, liquids of widely varying viscosity and density can be mixed without the use of mixing devices (for example, mechanical stirrers or rotary vane mixers) other than the present invention. Each outlet port is connected to a common outlet line for transmitting pressurized liquid medium to be injected into the patient.

Preferably, the pressurizing unit comprises at least three chambers. More preferably, the pressurizing unit comprises exactly three chambers. The present inventors have discovered that appropriately controlling the timing of the reciprocating motion of the pressurizing mechanism in each of three chambers enables control of the pump system to substantially reduce the pulsatile nature of flow commonly associated with pressurizing a liquid medium through reciprocal linear motion of a pressurizing mechanism.

The pump system preferably further comprises a drive mechanism in operative connection with the pressurizing mechanism of each chamber. The pressurizing unit is preferably readily releasable from connection with the drive mechanism. In this manner, those elements of the pump system which contact the liquid medium (that is, certain elements of the pressurizing unit) are easily removable for disposal or sterilization.

In a preferred embodiment, the chambers, inlet ports and outlet ports of the pressurizing unit are molded from an integral piece of polymeric material. Preferably, the chambers are in generally linear, side-by-side alignment in this embodiment. The pressurizing mechanism of each chamber preferably comprises a plunger or piston having a rearward extending member. The distal end of the extending member preferably extends beyond the rear of the chamber and comprises a cooperating connector (such as a flange) adapted to make a readily releasable connection of the extending member to the drive mechanism.

The present invention further provides a pump system for cooperating with a powered drive mechanism to inject a liquid medium into a patient. The pump system comprises a disposable pump unit. The disposable pump unit comprises at least two chambers. Each of chambers is attached to each other chamber in generally linear, side-by-side alignment. Each of the chambers has disposed therein a pressurizing mechanism to pressurize the liquid medium via generally linear motion of the pressurizing mechanism. The pressurizing mechanism of each chamber comprises a connector to releasable connect the pressurizing mechanism of each chamber to the powered drive mechanism.

The drive mechanisms of the pump systems of the present invention preferably comprises a timing mechanism to drive the pressurizing mechanism of each chamber in a timed fashion such that the flow rate and pressure of the liquid medium in the outlet line is substantially constant. In that regard, the degree of pulsatile flow (as such term is defined below) is preferably maintained below 25%.

The present invention also provides an injection system comprising one of the pump systems described above. Likewise, the present invention comprises a method of using the pumps systems described above for injection of a fluid medium into a patient. The pump systems and injection systems of the present invention deliver pressurized fluid from a low-pressure container continuously without having to stop and reload as required with conventional syringe pumps. The pump or pressurizing units of the present pump systems can be constructed out of inexpensive, easily molded plastic parts that can be assembled with few steps in a high-volume production operation. These inexpensive pump units can be discarded after a single use.

BRIEF DESCRIPTION OF THE DRAWINGS

FIG. 1A illustrates an embodiment of a pressurizing unit of the present invention.

FIG. 1B illustrates the pressurizing unit of FIG. 1A showing several subassemblies thereof.

FIG. 2A illustrates a partially cut-away view of the pressurizing unit of FIG. 1A showing the pressurizing mechanisms (pistons) within the chambers.

FIG. 2B illustrates a partially cut-away view of the pressurizing unit of FIG. 1A with the inlet and outlet channel portion and the pistons removed.

FIG. 8B illustrates the flow from pressurizing units comprising one, two, three, four and five cylinders.

DETAILED DESCRIPTION OF THE INVENTION

Figure 1C:
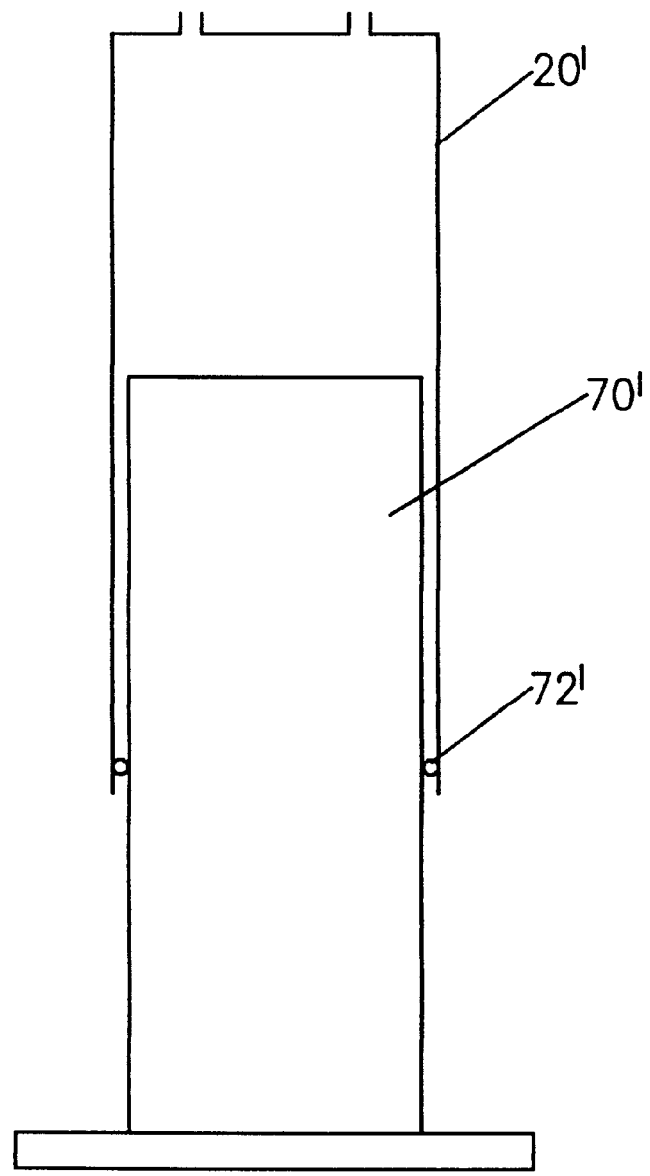
FIG. 1C illustrates a cross-sectional view of an alternative embodiment of a piston for use in a pressurizing unit of the present invention.
Figure 3:
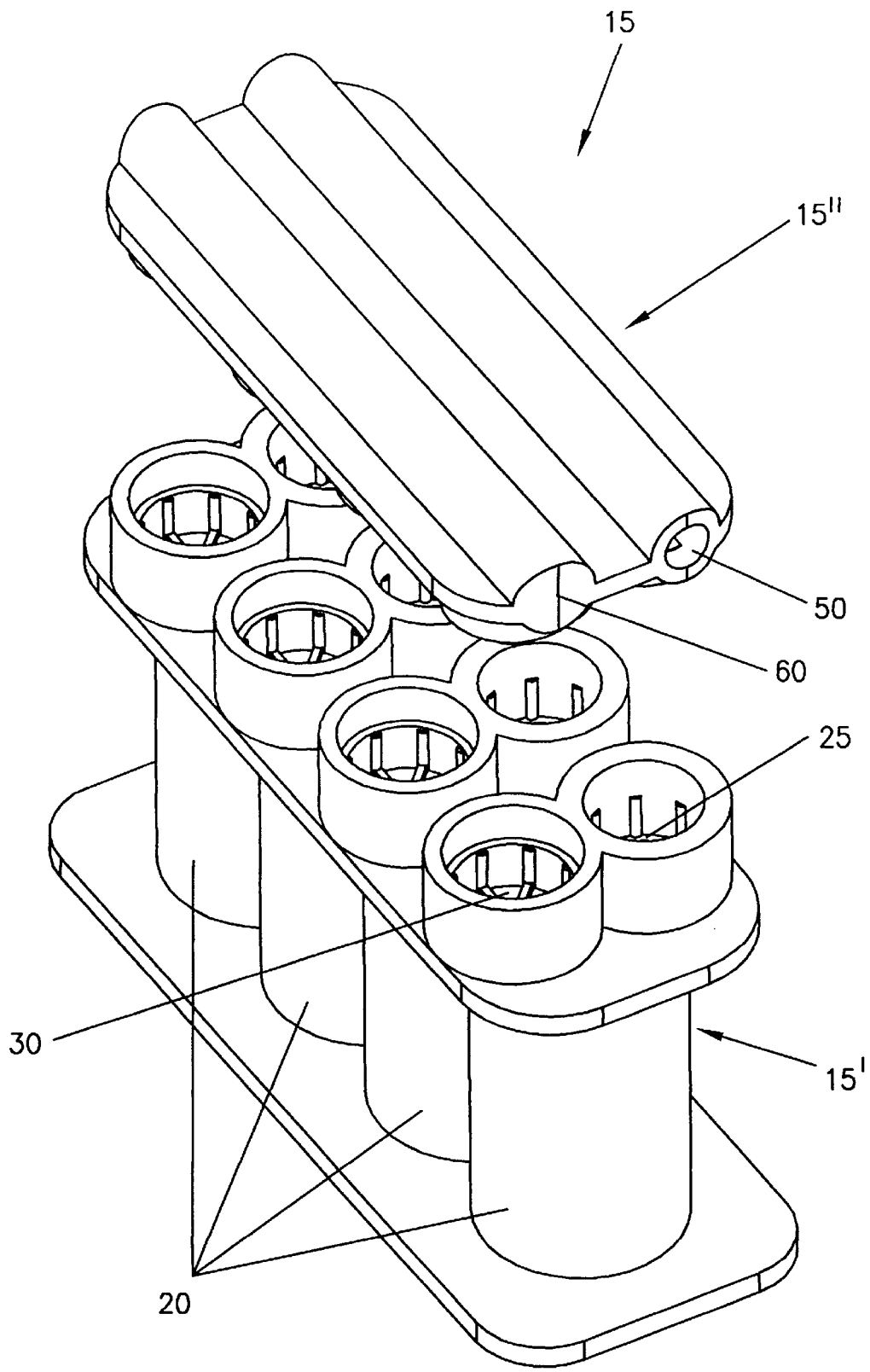
FIG. 3 illustrates a top perspective view of the pressurizing unit of FIG. 1A.
Figure 4:
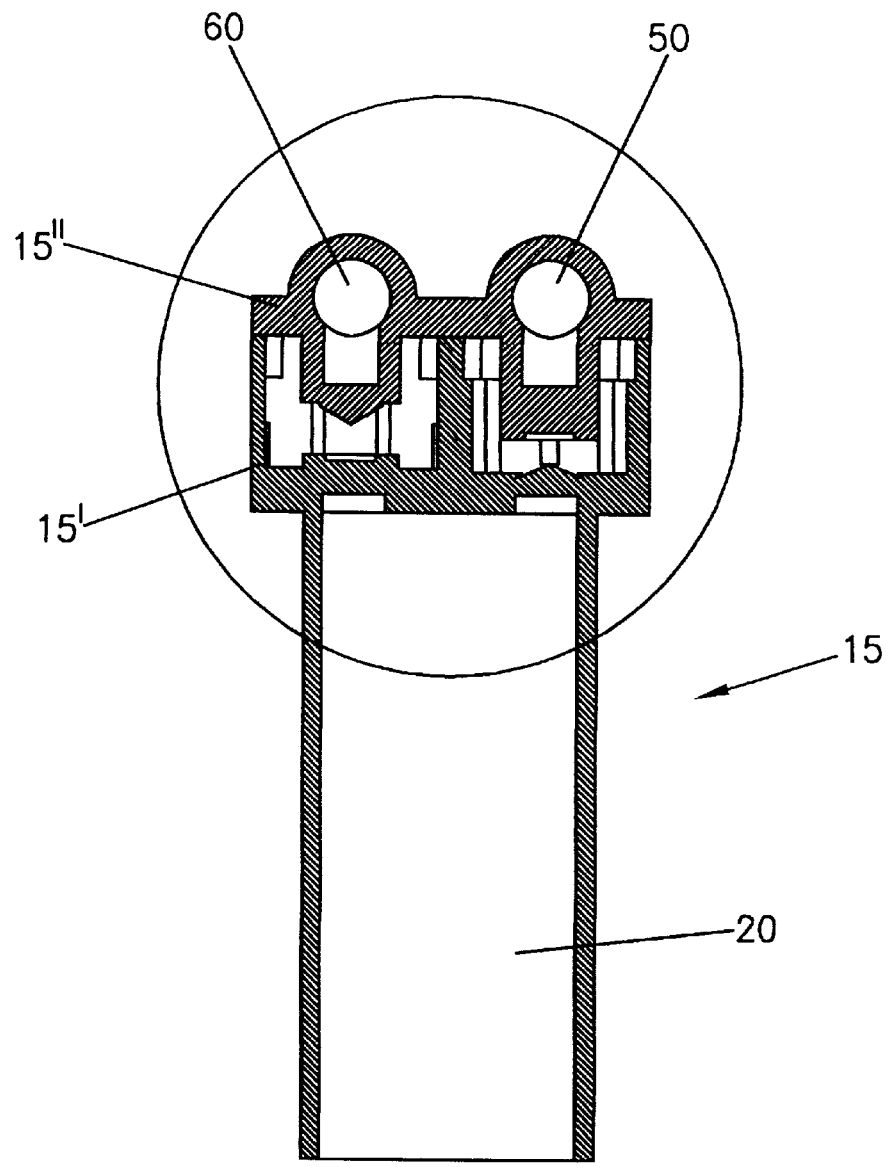
FIG. 4 illustrates a front, cross-sectional view of the pressurizing unit of FIG. 1A.
Figure 5:
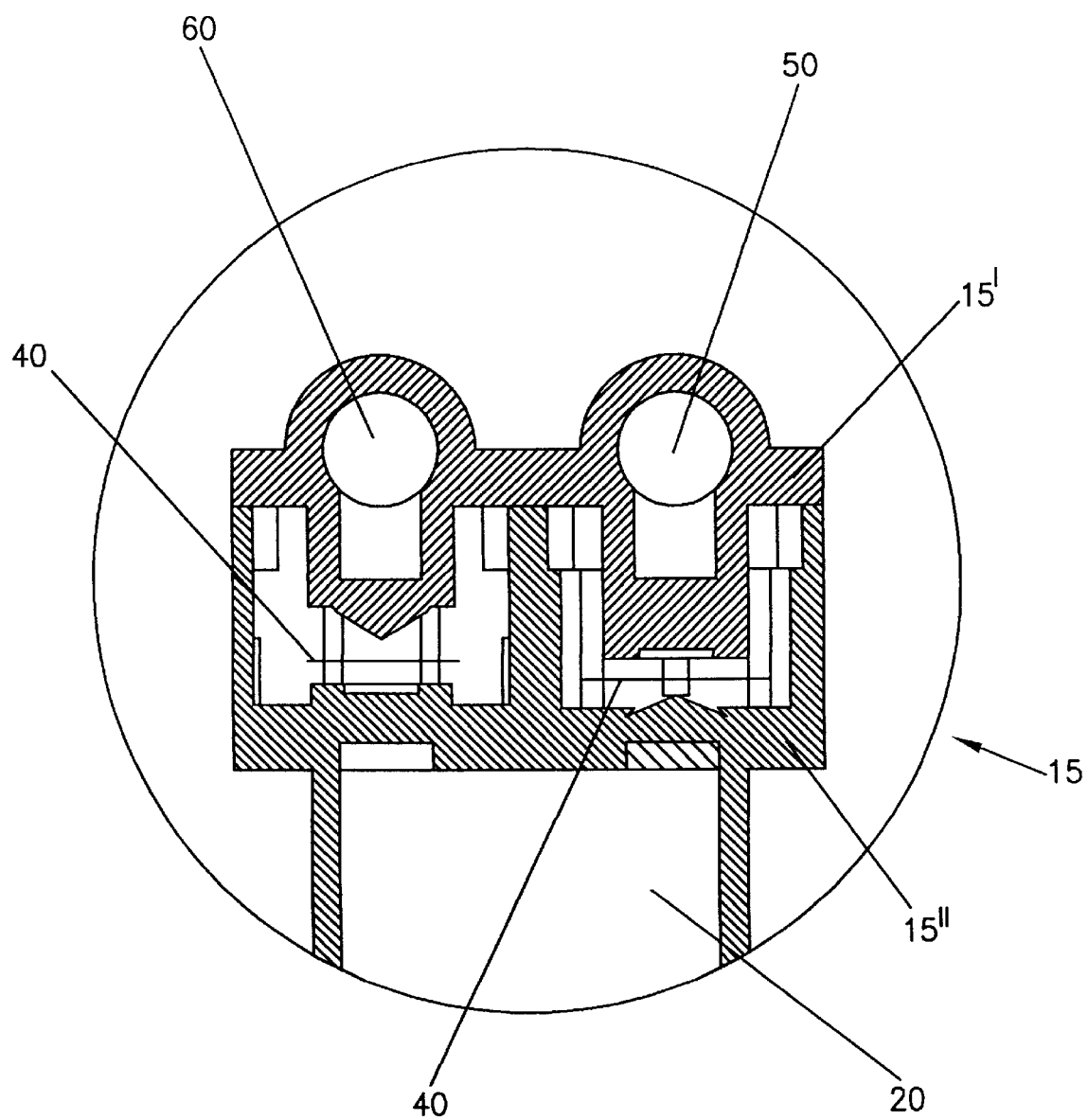
FIG. 5 illustrates an expanded, front cross-sectional view of an inlet port and outlet port of a single chamber.

FIGS. 1A through 7 illustrate one embodiment of a pump system 10 of the present invention. In this embodiment, four chambers 20 of pressurizing unit 15 are in generally linear, side-by-side alignment (that is, the axes of chambers 20 are generally in the same plane). Each chamber 15 comprises an inlet port 25 and an outlet port 30.

Inlet ports 25 and outlet ports 30 are preferably provided with check valves 40 to ensure the desired direction of flow is maintained. Inlet ports 25 are preferably in fluid connection with a common inlet channel 50, while outlet ports 30 are in fluid connection with a common outlet channel 60.

In this embodiment, pressurization unit 15 comprises a first or pump unit portion 15' and a second or head unit portion 15". First portion 15' comprises chambers 20, inlet ports 25 and outlet ports 30 and is preferably fabricated (for example, by injection molding) from an integral piece of polymeric material. Second portion 15" comprises inlet channel 50 and outlet channel 60. Like first portion 15', second portion 15" is preferably fabricated from an integral piece of polymeric material.

Check valves 40 may comprise, for example, flexible disks that act as valves to allow unidirectional flow into or out of each chamber 20. Flexible check valves 40 can be made of rubber or a lightweight polymer. Check valves 40 can be easily inserted into appropriately shaped receptacles and are preferably held in place when first portion 15' and second portion 15" are bonded together as known in the polymer arts.

Disposed within each chamber 20 is a piston 70 suitable to alternatively draw the liquid medium into chamber 20 upon a downward or rearward (that is, away from second portion 15") stroke thereof and pressurize the liquid medium, forcing the pressurized liquid medium into outlet channel 60, upon an upward or forward stroke thereof. Motive force is provided to pistons 70 by an external motor-driven drive mechanism 100 that imparts reciprocating linear motion to piston 70. High pressures in outlet channel 60 are possible with the proper choice of materials and wall thickness. For example, a pressure of approximately 800 psi is attainable in the case of polypropylene chambers having an inner diameter of approximately 0.476 inches and a wall thickness of approximately 0.042 inches.

In the illustrated embodiment, pistons 70 preferably comprise an elastomeric contact cover or surface 72. The circumference of contact surface 72 forms a sealing engagement with the sidewall of chamber 20. Contact surface 20 may be removably attachable to piston 70 via, for example, a flange 74. Piston 70 also preferably comprises a piston extension member 76 which extends rearward to exit chamber 20.

An alternative embodiment is illustrated in FIG. 1C. In this embodiment, piston 70' does not include a cover surface to contact the liquid medium. Rather, a sealing member such as an O-ring 72' is positioned between piston 70' and the inner wall of chamber 20'. As with piston 70, liquid medium is drawn into chamber 20' upon rearward motion of piston 70' and pressurized liquid medium is forced out of chamber 20' upon forward motion of piston 70'.

Figure 6B:
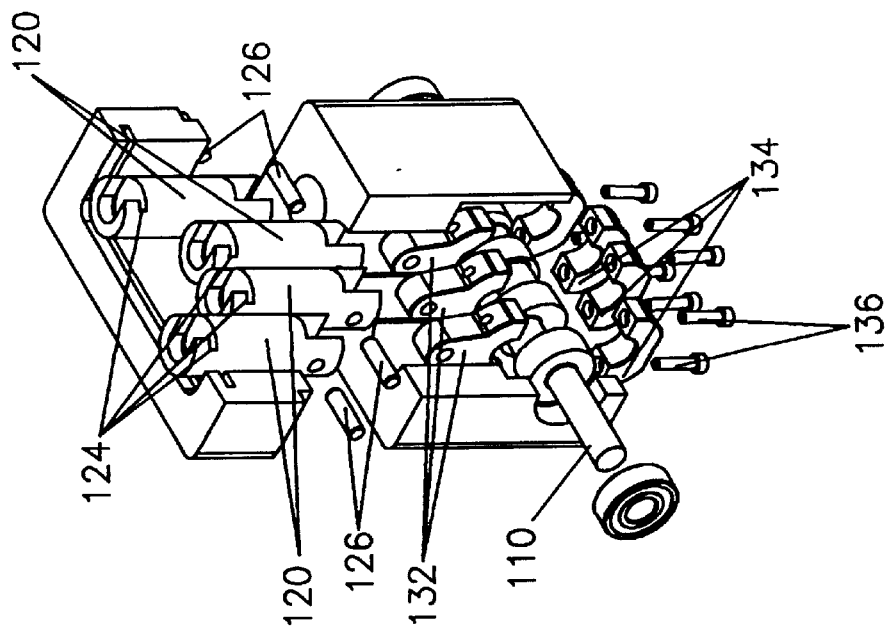
FIG. 6B illustrates a partially cut-away view of the drive mechanism of FIG. 6A showing several subassemblies thereof.
Figure 6A:
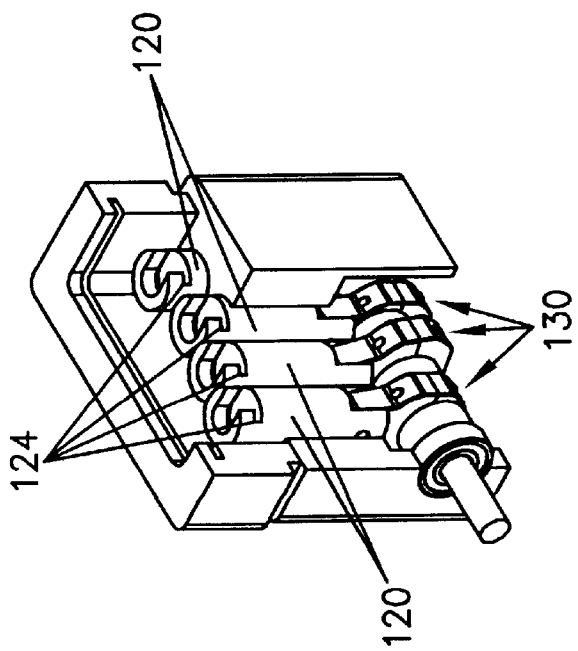
FIG. 6A illustrates a partially cut-away view of an embodiment of a drive mechanism for use with the pressurizing unit of FIG. 1.
Figure 6C:
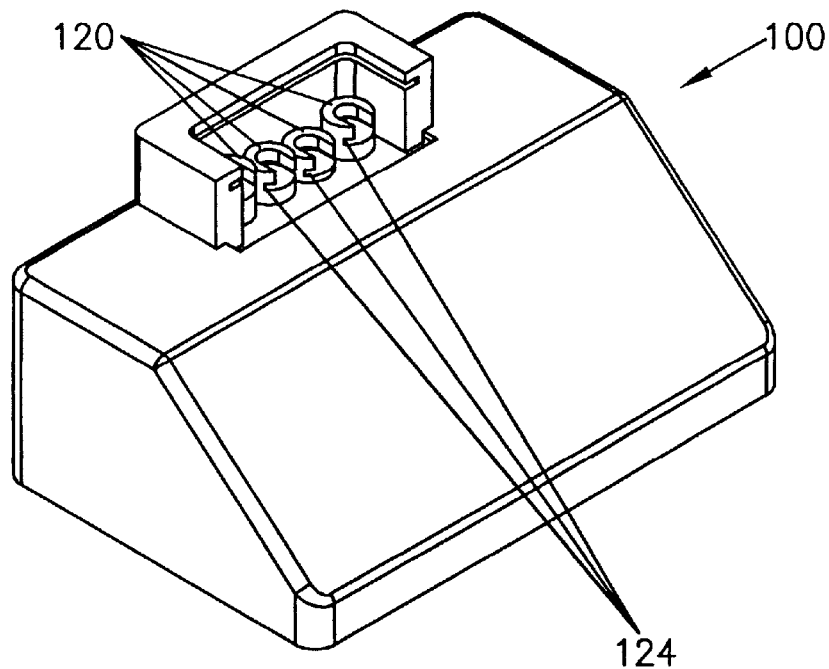
FIG. 6C illustrates a top perspective view of the drive mechanism of FIG. 6A.
Figure 6D:
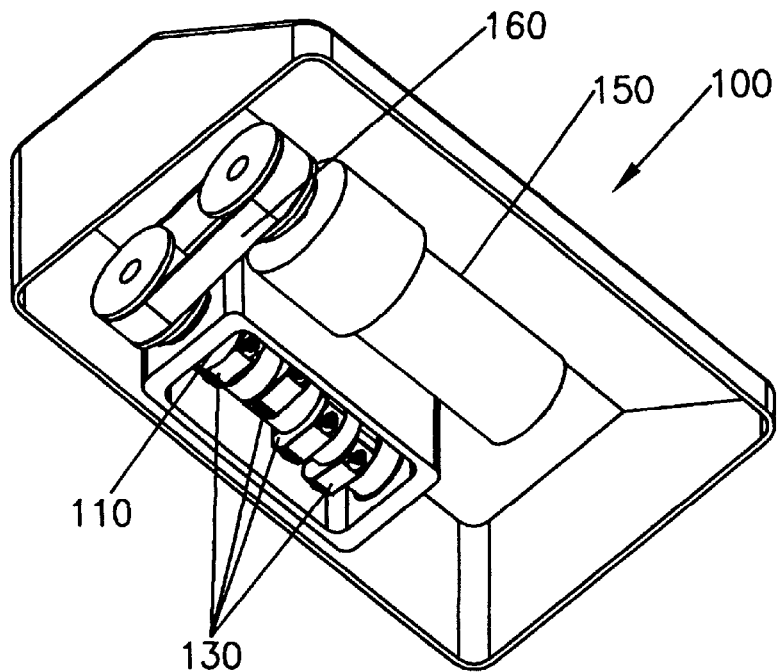
FIG. 6D illustrates a bottom perspective view of the drive mechanism of FIG. 6A.
Figure 7:
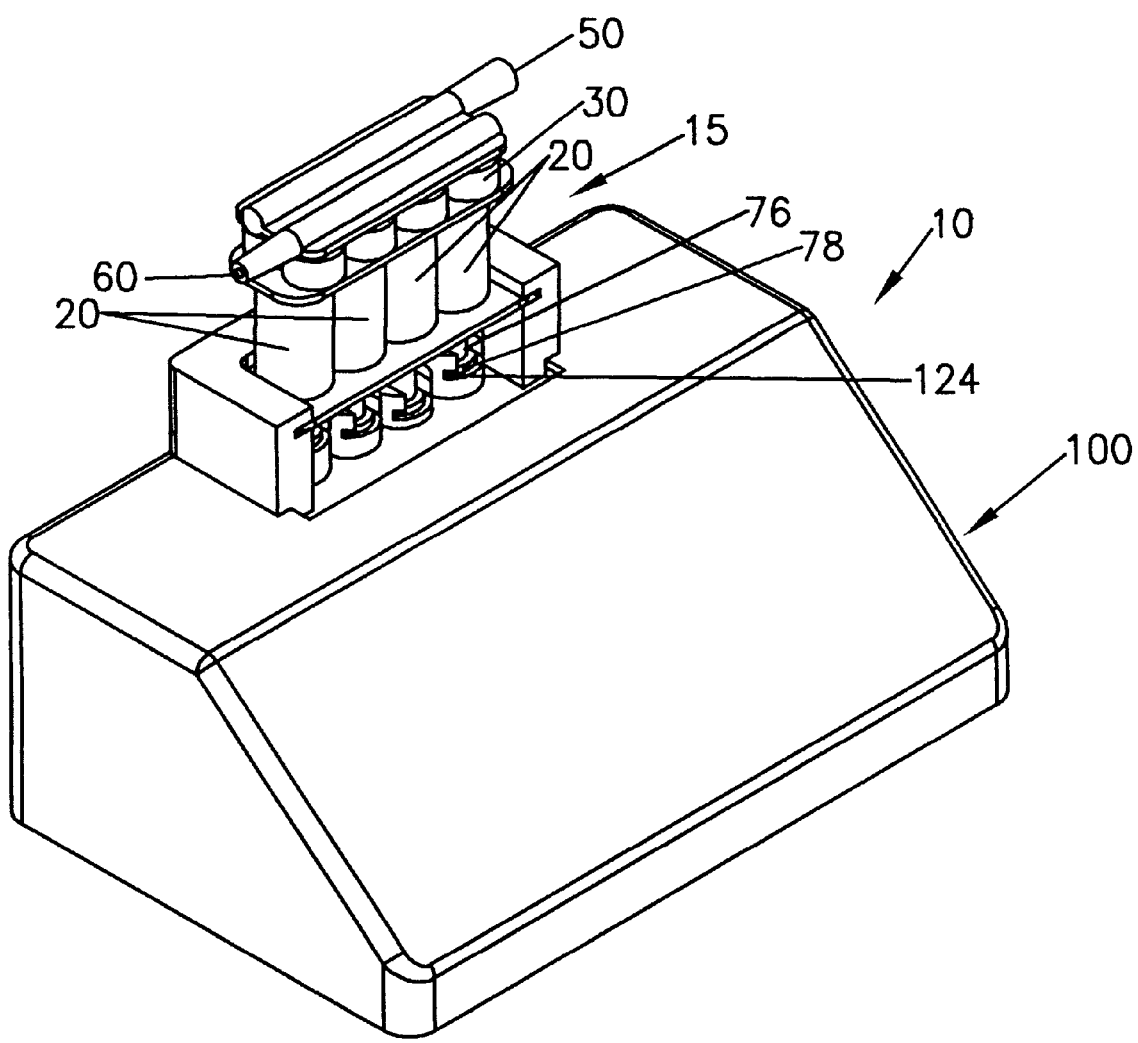
FIG. 7 illustrates a perspective view of a pump system comprising the pressurizing unit of FIG. 1 and the drive mechanism of FIGS. 6A through 6D in releasable connection.

Preferably, drive mechanism 100 comprises a cam shaft 110 which rotates to drive pistons 70 in a timed sequence chosen to reduce or substantially eliminate pulsatile flow. As illustrated in FIGS. 6A through 7, drive mechanism 100 preferably comprises drive extension members 120 which terminate on one end thereof in attachment members which cooperate with corresponding attachment members on piston extension members 76. As best illustrated in FIG. 7, slots 124 cooperate with flanges 78 to form a readily releasable connection between piston extension members 76 and drive extension members 120.

Drive extension members 120 are preferably attached to cam shaft 110 via bearing assemblies 130 and contacting pins 126. As illustrated in FIG. 6B bearing assemblies 130 preferably comprises a first bearing portion 132 and a second bearing portion 134 which are attached around cam shaft 110 via pins 136. As best illustrated in FIG. 6D, cam shaft 110 is preferably powered by a motor 150 via belt 160.

Figure 8A:
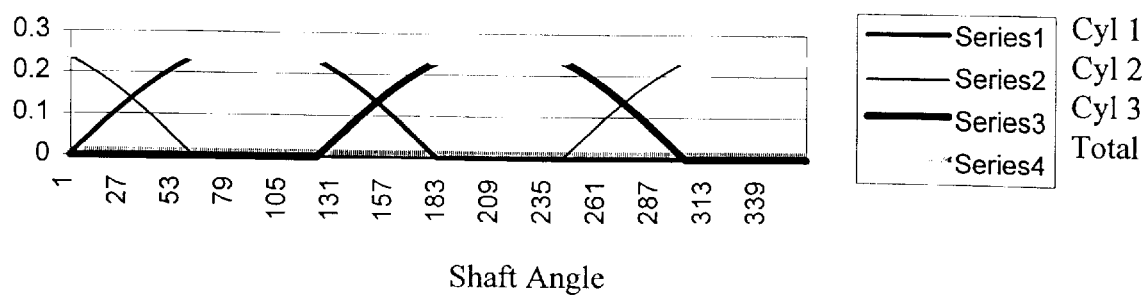
FIG. 8A illustrates the flow from each cylinder in a three-cylinder pressurizing unit as a function of shaft angle.

Several studies of the effect of the number of chambers 20 on the pulsatile nature of the flow are illustrated in FIGS. 8A and 8B. FIG. 8A illustrates the flow from each cylinder 20 as a function of shaft angle for three cylinders 20. The flow from each cylinder remains greater than 0 for only 180° of each 360° cycle. Flow less than 0 for any chamber is prevented because of check valves 40. The three flow curve (a, b and c) are summed together. In general, the flow rate (as a function of time in seconds) is provided by the following equations:

$$\text{Flow}(t) = K * \{pos(\sin \omega t) + pos(\sin[\omega t + 120]) + pos(\sin[\omega t - 120])\}$$

wherein K is a constant;

pos designates that only the positive part of each sine wave is added; and

ω is the rate of rotation in degrees per second.

In the present calculations, K was chosen to be 0.8. The average flow rate (avg flow) per 360-degree cycle can be shown to be $K/\pi = 0.254$. The average flow (that is, the area under the "sum of the components" curve) was set to be the same for each study. The maximum flow rate (max flow) and minimum flow rate (min flow) vary based on this normalization. A degree or percent of pulsatile flow can be defined with the following equation:

$$100\% * (\text{max flow} - \text{min flow})/\text{average flow}$$

Table 1 summarizes the results obtained for one through five chambers 20. These results are illustrated graphically in FIG. 8B.

TABLE 1

| Chambers | Avg. Flow | Min Flow | Max Flow | Degree of Pulsatile Flow |
|---|---|---|---|---|
| 1 | .254 | 0 | .8 | 315% |
| 2 | .254 | 0 | .4 | 157% |
| 3 | .254 | .236 | .271 | 14% |
| 4 | .254 | .203 | .283 | 31% |
| 5 | .254 | .249 | .261 | 5% |

Preferably, the degree of pulsatile flow is maintained at or below 25%. At or below such a degree of pulsatile flow, the pulsatile nature of the flow is considered to be minimal for the purpose of the present invention. More preferably, the degree of pulsatile flow is maintained at or below 20%. The present inventors have discovered that with a minimum of three chambers 20 it is possible to develop a substantially steady fluid flow with minimal pulsatile component. Surprisingly, four chamber 20 are shown to have a greater degree of pulsatile flow than three chambers 20. In general, beyond four chambers 20, the degree of pulsatile flow continues to decrease. Adding more chambers 20 may allow a higher flow rate to be achieved with a shorter piston stroke length in each chamber 20. Additional chambers 20 may thus reduce wear and extend lifetime of pump system 10.

While providing greater than three chambers 15 may increase the lifetime of pressurizing unit 15, it also increases manufacturing costs and manufacturing difficulty. It is desirable, however, to minimize the costs of pressurizing unit 15 in part so that pressurizing unit 15 (or at least those elements of pressurizing unit 15 that contact the liquid medium) may be discarded after use with a single patient. Disposal of pressurizing unit 15 after use with a single patient reduces the likelihood of cross-patient contamination. As three chambers 20 enable flow with a minimal pulsatile component at a minimum manufacturing cost, pressurizing unit 15 preferably comprises three chambers 20. Additionally, for any number of chambers 20, the degree of pulsatile flow can be decreased or substantially eliminated by including a damping chamber 660 (see FIG. 11) in fluid connection with outlet channel 60. In general, such damping chambers have a mechanical capacitance provided by some type of distending member such as a balloon or bladder. An example of a damping chamber suitable for use in the present invention is the FMI Pulse Dampener Model PD-60-LS or Model PD-HF available from Fluid Metering, Inc. of Oyster Bay, N.Y.

Figure 9:
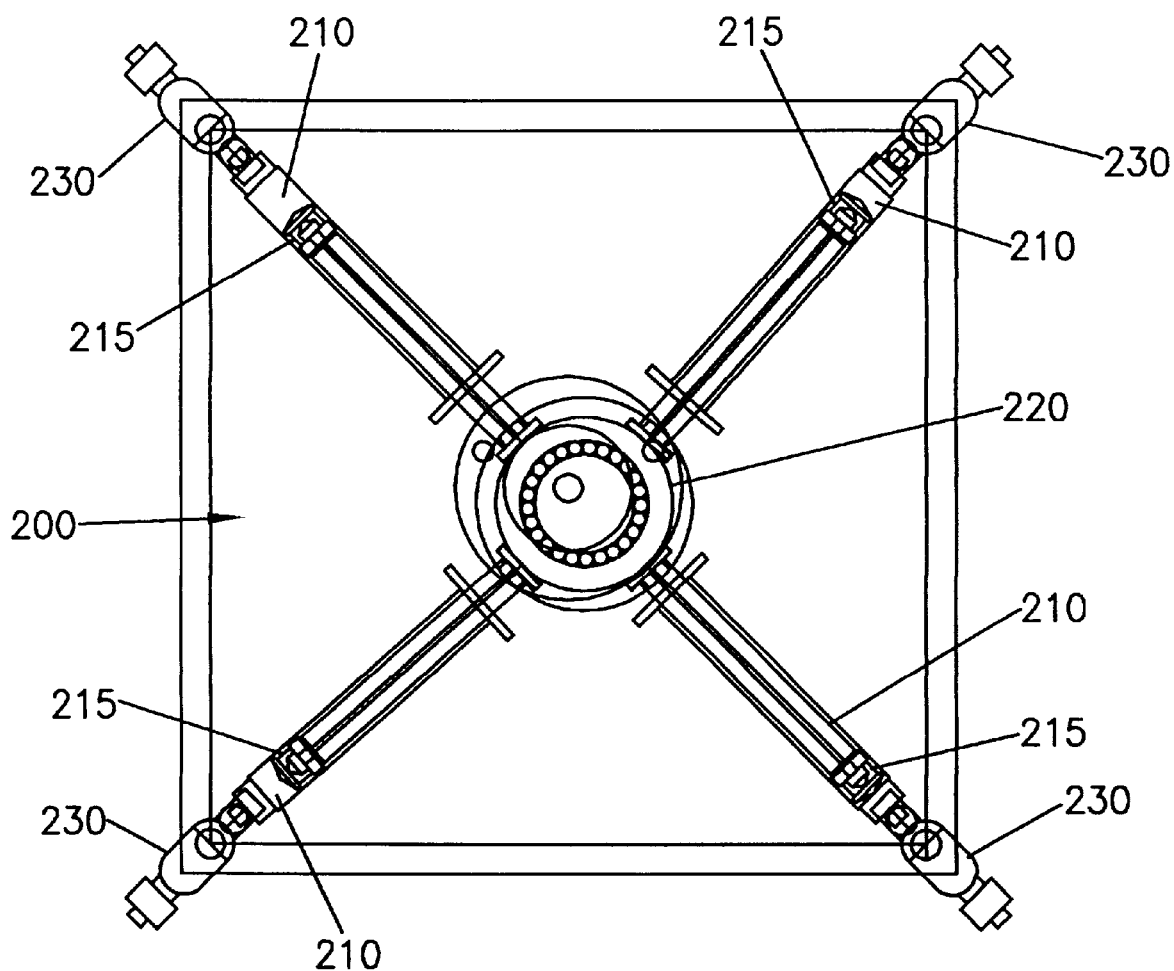
FIG. 9 illustrates an embodiment of a pump system in which the chambers are distributed radially around the drive mechanism.
Figure 10:
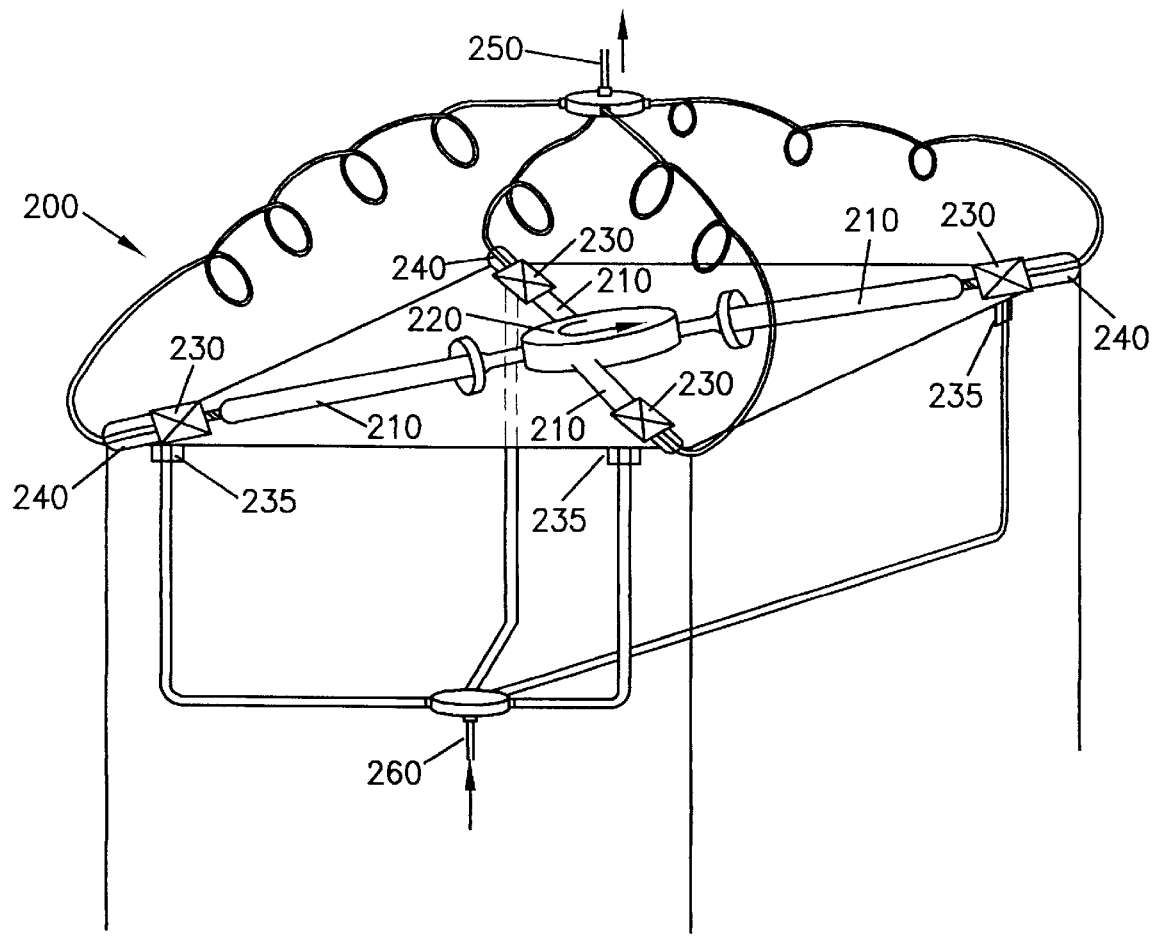
FIG. 10 illustrates the pumping system of FIG. 9 in which the inlet ports are connectable to a common source of liquid medium and the outlet ports are connected to a common outlet line.

As illustrated in FIGS. 9 and 10, in another embodiment of a pump system 200 of the present invention, chambers 210 (four are shown) are configured generally radially and symmetrically about a common center. Each chamber 210 comprises a reciprocating piston or plunger 215, the operation of which is essentially the same as discussed in connection with pump system 10. In pump system 200, however, each piston 215 is preferably driven by an eccentric cam 220 to which each piston 215 is releasably connected. As cam 220 rotates, each piston 215 is pushed or pulled in a desired sequence to provide continuous flow. A check valve system 230 is connected to each chamber 210 to substantially ensure that the liquid medium enters chamber 210 via inlet port 235, but cannot exit chamber 210 via inlet port 235. Likewise, check valve system 235 substantially ensures that the liquid medium exits chamber 210 via outlet port 240, but cannot enter chamber 210 via outlet port 240. All outlet ports 240 are in fluid connection with a common outlet channel 250. Inlet ports 235 can be connected to a common inlet channel 260.

Figure 11:
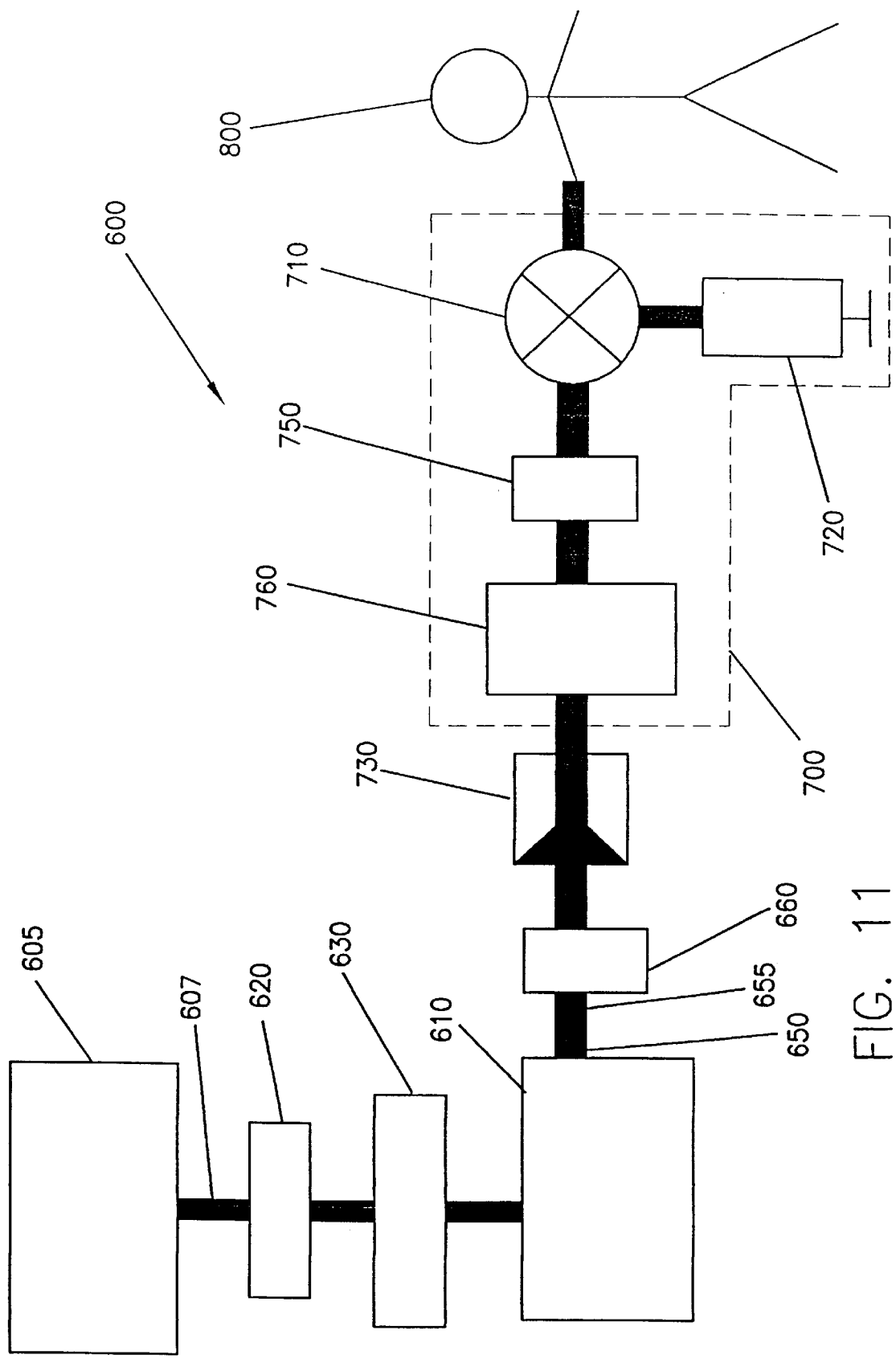
FIG. 11 illustrates an embodiment of an injection system of the present invention.

As illustrated in the FIG. 11, the present invention also provides an injection system 600 comprising a pump system 610 as described above. Injection systems well suited for use with the pump systems of the present invention are discussed in U.S. patent application Ser. Nos. 08/144,845 and 08/655,886, the disclosures of which is incorporated herein by reference. As illustrated in FIG. 11, injection system 600 preferably comprises at least one liquid medium container 605 in fluid connection with pump system 610 via line 607. Preferably, a mechanism for detecting air bubbles 620 and/or a mechanism for removing such air bubbles 630 are placed in fluid connection with the medium container before pump system 610 such that the air bubbles are removed from the medium before the medium reaches pump system 610. Detection mechanism 620 can, for example, be an ultrasonic sensor such as available from Zevex of Salt Lake City, Utah or Introtech of Edgewood, N.Y. Air-eliminating filters suitable for use in the present invention as air removing mechanism 630 are available, for example, from Gelman Sciences, Inc. of Ann Arbor, Mich. Air removing mechanism 630 may also comprise a Gore-Tex® PTFE Membrane Vent available from W.L. Gore & Associates, Inc of New Jersey. Because such systems often cannot detect or remove small air bubbles and consequently do not operate well at high pressure, detection means 620 and/or removing means 630 are preferably located before pump system 610 so that any bubbles within the fluid stream will be as large as possible.

Injection system 600 also preferably includes (in fluid connection with outlet port 650 of the pump system 610 via line 655) a disposable patient interface 700 in contact with a patient 800 for injection of the medium into patient 800. As discussed above, a dampening chamber 660 may be placed in fluid connection with outlet port 650 to further minimize or substantially eliminate the degree of pulsatile flow. Connector tubes commonly used in the medical arts may also act to reduce the degree of pulsatile flow because of their compliance. Patient interface preferably includes a three-way stopcock 710 and a hand-operated syringe 720. In connection with stopcock 710, syringe 720 may be used to draw blood from the patient, for example, to verify good intravenous catheter placement in CT and to purge any small bubbles of air that might occur connection 710 with the vascular catheter. Syringe 720 may also be used to inject fluids other than the medium (for example, medications). Further, syringe 720 can be filled with medium for test injections during angiography. Patient interface 700 is preferably disposed of after each procedure.

Before reaching patient interface 700, the output of pump system 610 is preferably in fluid connection with a check valve 730 for substantially ensuring unidirectional flow of the medium and thereby substantially preventing contamination of pump system 610 with body fluids. Check valve 730 may comprise, for example, a spring-loaded ball valve or a duck bill valve. The need for check valve 730 may be eliminated by providing the pump system drive mechanism with a mechanism for preventing reverse rotation thereof. For example, the drive shaft of pump system 610 can be provided with detentes or stops (not shown) to prevent reverse rotation. In any event, check valves 40 prevent reverse flow independent of the direction of rotation. Prior to reaching patient interface 700, the effluent of pump system 610 is preferably in fluid connection with a mechanism 750 for removing particles from the medium.

In certain embodiments it may be desirable to include a mechanism 760 for limiting or stopping flow of the injection medium if the developed pressure exceeds a certain threshold pressure, for example, to prevent failure of the intravascular catheter. This result can be accomplished in a number of manners including the inclusion of a mechanism for sensing pressure in connection with the outlet of pump system 610. A mechanism for sensing motor current of the drive mechanism motor can also be provided as an indirect measurement of pressure.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A pump system for pressurizing a liquid medium for injection into a patient, the pump system comprising: at least two chambers, each chamber having disposed therein a pressurizing mechanism comprising an extending member to pressurize the liquid medium within the chamber; and a drive mechanism in operative connection with the extending members of the pressurizing mechanisms, the drive mechanism comprising timing means for driving the extending members of each pressurizing mechanism in a timed fashion to reduce the pulsatile nature of the flow in an outlet line, each chamber further comprising a separate inlet port and a separate outlet port, each inlet port being connected to a liquid medium source, each outlet port being connected to the outlet line, for transmitting pressurized liquid medium to the patient, wherein each pressurizing member is reciprocally driven by the drive mechanism to inject the liquid medium into the patient.

2. The pump system of claim 1 wherein the drive mechanism is readily removable from connection with the pressurizing mechanism of each chamber.

3. The pump system of claim 1 wherein the pressurizing mechanism and chambers are disposable.

4. The pump system of claim 1 wherein the chambers, inlet ports and outlet ports are molded from an integral piece of polymeric material.

5. The pump system of claim 1 wherein the chambers are in generally linear, side-by-side alignment.

6. The pump system of claim 5 wherein the pump system comprises three chambers.

7. The pump system of claim 2 wherein the pressurizing mechanism further comprises a piston, and further wherein the extending member comprises a connector on a distal end thereof to releasably connect the extending member to the drive mechanism.

8. The pump system of claim 1 wherein the inlet port of each chamber is connected to a common source of liquid medium.

9. The pump system of claim 1 wherein the inlet port of one chamber is connected to a first liquid medium container containing a first liquid medium and the inlet port of at least one other chamber is connected to a second liquid medium container containing a second liquid medium which is different from the first liquid medium to effect mixing of the first liquid medium and the second liquid medium.

10. The pump system of claim 1 further comprising a dampening chamber in fluid connection with the common outlet line.

11. An injection system for injecting a liquid medium into a patient, the injection system comprising:
   a. at least one liquid medium container;
   b. a pump system in fluid connection with the at least one liquid medium container, the pump system comprising at least two chambers, each chamber having disposed therein a pressurizing mechanism comprising an extending member to pressurize the liquid medium within the chamber, and a drive mechanism in operative connection with the extending members of the pressurizing mechanisms, the drive mechanism comprising timing means for driving the extending members of the pressurizing mechanisms in a timed fashion to reduce the pulsatile nature of the flow in an outlet line, each chamber further comprising a separate inlet port and a separate outlet port, each inlet port being connected to the at least one liquid medium container, each outlet port being connected to the outlet line for transmitting pressurized liquid medium to the patient, wherein each pressurizing member is reciprocally driven by the drive mechanism to inject the liquid medium into the patient; and
   c. a disposable patient interface in contact with the patient for injection of pressurized liquid medium into the patient, the disposable patient interface being in fluid connection with the outlet line.

12. The injection system of claim 11 wherein the drive mechanism is readily removable from connection with the pressurizing mechanism of each chamber.

13. The injection system of claim 12 wherein the pressurizing mechanism further comprises a piston, and further wherein the extending member comprises a connector on a distal end thereof to releasably connect the extending member to the drive mechanism.

14. The injection system of claim 11 wherein the pressurizing mechanism and chambers are disposable.

15. The injection system of claim 11 wherein the chambers, inlet ports and outlet ports are molded from an integral piece of polymeric material.

16. The injection system of claim 11 wherein the chambers are in generally linear, side-by-side alignment.

17. The injection system of claim 16 wherein the pump system comprises three chambers.

18. The injection system of claim 11 wherein the inlet port of each chamber is connected to one liquid medium container.

19. The injection system of claim 11 wherein the inlet port of one chamber is connected to a first liquid medium container containing a first liquid medium and the inlet port of at least one other chamber is connected to a second liquid medium container containing a second liquid medium which is different from the first liquid medium to effect mixing of the first liquid medium and the second liquid medium.

20. The injection system of claim 11 further comprising a dampening chamber in fluid connection with the common outlet line.

21. A pump system for cooperating with a powered drive mechanism to inject a liquid medium into a patient, the pump system comprising a disposable pump unit, the disposable pump unit comprising at least two chambers, each of the chambers having disposed therein a pressurizing mechanism to pressurize the liquid medium, the pressurizing mechanism of each chamber comprising an extending member having a connector to releasably connect the pressurizing mechanism of each chambers to timing means of the powered drive mechanism, the timing means driving the extending members of the pressurizing mechanisms in a timed fashion to reduce the pulsatile nature of the flow in a separate outlet line of the pump unit, wherein each pressurizing member is reciprocally driven by the drive mechanism to inject the liquid medium into the patient.

22. The pump system of claim 21 wherein the disposable pump unit comprises three chambers.

23. The pump system of claim 21 wherein each chamber further comprising an inlet port and an outlet port, the inlet port of each chamber being in fluid connection with an inlet port check valve adapted to allow the liquid medium to flow into the chamber through the inlet port and to substantially prevent the liquid medium from flowing out of the chamber through the inlet port, the outlet port of each chamber being in fluid connection with an outlet port check valve adapted to allow pressurized liquid medium to flow out of the chamber through the outlet port and to substantially prevent the liquid medium from flowing into the chamber through the outlet port, each inlet port being connected to a liquid medium source, each outlet port being connected to a common outlet line for transmitting pressurized liquid medium to the patient.

24. The pump system of claim 21 wherein the disposable pumping unit is molded from an integral piece of polymeric material.

25. The pump system of claim 21 wherein the disposable pump unit comprises an integral head unit comprising a common channel in fluid connection with the common outlet line and a common inlet line in fluid connection with the liquid medium source and with each inlet port.

26. The pump system of claim 21 wherein the disposable pump unit comprises an integral head unit comprising the common outlet channel in fluid connection with the common outlet line and a first inlet channel, the first inlet channel being connected to a first liquid medium container containing a first liquid medium, the inlet port of one chamber being in fluid connection with the first inlet channel to receive the first liquid medium from the first liquid medium container, the head unit further comprising a second inlet channel, the second inlet channel being in fluid connection with a second liquid medium container containing a second liquid medium which is different from the first liquid medium, the inlet port of another chamber being in fluid connection with the second inlet channel to receive the second liquid medium from the second liquid medium source and to thereby effect mixing of the first liquid medium and the second liquid medium.

27. A method of using a pump system for injecting a liquid medium into a patient, comprising the following steps: providing a powered drive mechanism; providing a disposable pump unit comprising at least two chambers, each of the chambers being attached to each other chamber in generally linear, side-by-side alignment, each chamber having disposed therein a pressurizing mechanism to pressurize the liquid medium via generally linear motion of the pressurizing mechanism, the pressurizing mechanism of each chamber comprising a connector to releasably connect the pressurizing mechanism of each chamber to the powered drive mechanism, each chamber further comprising an inlet port and an outlet port, the inlet port of each chamber being in fluid communication with an inlet port check valve adapted to allow the liquid medium to flow into the chamber through the inlet port and to substantially prevent the liquid medium from flowing out of the chamber through the inlet port, the outlet port of each chamber being in fluid communication with an outlet port check valve adapted to allow pressurized liquid medium to flow out of the chamber through the outlet port and to substantially prevent the liquid medium from flowing into the chamber through the outlet port, each inlet port being connected to a liquid medium source, each outlet port being connected to a common outlet line for transmitting pressurized liquid medium to the patient;

releasably connecting the disposable pump unit to the drive mechanism; and driving the pressurizing mechanism of each chamber via the drive mechanism in a timed fashion such that the flow rate and pressure of the liquid medium in the outlet line remain substantially constant.

28. The method of claim 27, further comprising the steps of:

providing a patient interface having a first end and a second end;

connecting the first end of the patient interface to the outlet line; and connecting the second end of the patient interface to the patient.

29. A pump for cooperating with a powered drive mechanism to inject a liquid medium into a patient, the pump comprising at least two chambers, each of the chambers having disposed therein a pressurizing mechanism to pressurize the liquid medium, the pressurizing mechanism of each chamber comprising an extending member having a connector to releasably connect the pressurizing mechanism of each chamber to timing means of the powered drive mechanism, the timing means driving the extending members of the pressurizing mechanisms in a timed fashion such that the flow rate and pressure of the liquid medium in separate outlet line remain substantially constant, wherein each pressurizing member is reciprocally driven by the drive mechanism to inject the liquid medium into the patient.

30. A method of using a pump system for injecting a liquid medium into a patient, comprising the following steps:

providing a powered drive mechanism;

providing a disposable pump unit comprising at least three chambers, each of the chambers having disposed therein a pressurizing mechanism to pressurize the liquid medium via generally linear motion of the pressurizing mechanism, the pressurizing mechanism of each chamber comprising a connector to releasably connect the pressurizing mechanism of each chamber to the powered drive mechanism, each chamber further comprising an inlet port and an outlet port, the inlet port of each chamber being in fluid communication with an inlet port check valve adapted to allow the liquid medium to flow into the chamber through the inlet port and to substantially prevent the liquid medium from flowing out of the chamber through the inlet port, the outlet port of each chamber being in fluid communication with an outlet port check valve adapted to allow pressurized liquid medium to flow out of the chamber through the outlet port and to substantially prevent the liquid medium from flowing into the chamber through the outlet port, each inlet port being connected to a liquid medium source, each outlet port being connected to a common outlet line for transmitting pressurized liquid medium to the patient;

releasably connecting the disposable pump unit to the drive mechanism; and driving the pressurizing mechanism of each chamber via the drive mechanism in a timed fashion such that the flow rate and pressure of the liquid medium in the outlet line remain substantially constant.

31. The method of claim 30, further comprising the steps of:

providing a patient interface having a first end and a second end;

connecting the first end of the patient interface to the outlet line; and connecting the second end of the patient interface to the patient.

32. A method of injecting a liquid medium into a patient, comprising the following steps:

providing a drive mechanism comprising timing means;

providing a pump unit comprising at least two chambers, each of the chambers having disposed therein a pressurizing mechanism to pressurize the liquid medium, the pressurizing mechanism of each chamber comprising an extending member having a connector to connect the pressurizing mechanism of each chamber to the timing means of the drive mechanism, each chamber further comprising a separate inlet port and a separate outlet port, each inlet port being connected to a liquid medium source, each outlet port being connected to an outlet line for transmitting pressurized liquid medium to the patient;

connecting the pump unit to the drive mechanism; and driving the extending members of the pressurizing mechanisms of each chamber via the timing means of the drive mechanism in a timed fashion such that the flow rate and pressure of the liquid medium in the outlet line remain substantially constant, wherein each pressurizing member is reciprocally driven by the drive mechanism to inject the liquid medium into the patient.

33. The method of claim 32 wherein said connecting step comprises releasably connecting the pump unit to the drive mechanism.

34. The method of claim 32, further comprising the steps of:

providing a patient interface having a first end and a second end;

connecting the first end of the patient interface to the outlet line; and connecting the second end of the patient interface to the patient.

35. A pump system for use in pressurizing a liquid medium for injection into a patient, the pump system comprising at least three chambers, each chamber having disposed therein a pressurizing mechanism comprising an extending member to pressurize the liquid medium, the pressurizing mechanism pressurizing the liquid medium via generally linear motion of the pressurizing mechanism within the chamber; and a drive mechanism in operative connection with the extending members of the pressurizing mechanisms, the drive mechanism comprising timing means for driving the extending members of the pressurizing mechanisms in a timed fashion to reduce the pulsatile nature of the flow in an outlet line, each chamber further comprising an inlet port and an outlet port, each inlet port being in fluid connection with an inlet port check valve adapted to allow the liquid medium to flow into the chamber through the inlet port and to substantially prevent the liquid medium from flowing out of the chamber through the inlet port, each outlet port being in fluid connection with an outlet port check valve adapted to allow pressurized liquid medium to flow out of the chamber through the outlet port and to substantially prevent the liquid medium from flowing into the chamber through the outlet port, each inlet port being connected to a liquid medium source, each outlet port being connected to a common outlet line for transmitting pressurized liquid medium to the patient.

36. An injection system for use in injecting a liquid medium into a patient, the injection system comprising:

at least one liquid medium container;

a pump system in fluid connection with the at least one liquid medium container, the pump system comprising at least three chambers, each chamber having disposed therein a pressurizing mechanism comprising an extending member to pressurize the liquid medium, the pressurizing mechanism pressurizing the liquid medium via generally linear motion of the pressurizing mechanism within the chamber, and a drive mechanism in operative connection with the extending members of the pressurizing mechanisms, the drive mechanism comprising timing means for driving the extending members of the pressurizing mechanisns in a timed fashion to reduce the pulsatile nature of the flow in an outlet line, each chamber further comprising an inlet port and an outlet port, the inlet port of each chamber being in fluid connecting with an inlet port check valve adapted to allow the liquid medium to flow into the chamber through the inlet port and to substantially prevent the liquid medium from flowing out of the chamber through the inlet port, the outlet port of each chamber being in fluid connection with an outlet port check valve adapted to allow pressurized liquid medium to flow out of the chamber through the outlet port and to substantially prevent the liquid medium from flowing into the chamber through the outlet port, each inlet port being connected to the at least one liquid medium container, each outlet port being connected to a common outlet line for transmitting pressurized liquid medium to the patient; and a disposable patient interface in contact with the patient for injection of pressurized liquid medium into the patient, the disposable patient interface being in fluid connection with the common outlet line.

37. A pump system for cooperating with a powered drive mechanism to inject a liquid medium into a patient, the pump system comprising a disposable pump unit, the disposable pump unit comprising at least two chambers, each of the chambers being attached to each other chamber in generally linear, side-by-side alignment, each of the chambers having disposed therein a pressurizing mechanism to pressurize the liquid medium via reciprocal motion of the pressurizing mechanism, the pressurizing mechanism of each chamber comprising an extending member having a connector to releasably connect the pressurizing mechanism of each chamber to timing means of the powered drive mechanism, the timing means driving the extending members of the pressuring mechanisms in a timed fashion to reduce the pulsatile nature of the flow in a separate outlet line of the pump unit.

38. A pump for cooperating with a powered drive mechanism to inject a liquid medium into a patient, the pump comprising at least three chambers, each of the chambers having disposed therein a pressurizing mechanism to pressurize the liquid medium via reciprocal motion of the pressurizing mechanism, the pressurizing mechanism of each chamber comprising an extending member having a connector to releasably connect the pressurizing mechanism of each chamber to timing means of the powered drive mechanism, the timing means driving the extending members of the pressurizing mechanisms in a timed fashion such that the flow rate and pressure of the liquid medium in a separate outlet line remain substantially constant.

* * * * *